United States Patent
Juhasz et al.

(12) 
(10) Patent No.: US 6,254,595 B1
(45) Date of Patent: Jul. 3, 2001

(54) CORNEAL APLANATION DEVICE

(75) Inventors: Tibor Juhasz; Ronald M. Kurtz, both of Irvine, CA (US)

(73) Assignee: Intralase Corporation, Irvine, CA (US)

( * ) Notice: Subject to any disclaimer, the term of this patent is extended or adjusted under 35 U.S.C. 154(b) by 0 days.

(21) Appl. No.: 09/172,819

(22) Filed: Oct. 15, 1998

(51) Int. Cl.[7] .................................................. A61B 18/20
(52) U.S. Cl. ................................................. 606/5; 606/17
(58) Field of Search ................................ 606/1, 4, 5, 17; 607/80, 88, 89; 359/708

(56) References Cited

U.S. PATENT DOCUMENTS

| | | |
|---|---|---|
| 4,665,913 | 5/1987 | L'Esperance, Jr. . |
| 4,669,466 | 6/1987 | L'Esperance . |
| 4,712,543 | 12/1987 | Baron . |
| 4,718,418 | 1/1988 | L'Esperance . |
| 4,729,372 | 3/1988 | L'Esperance, Jr. . |
| 4,732,148 | 3/1988 | L'Esperance, Jr. . |
| 4,772,115 | 9/1988 | Gersten et al. . |
| 4,856,513 | 8/1989 | Muller . |
| 4,905,711 | 3/1990 | Bennett et al. . |
| 4,907,872 | 3/1990 | Schirmer . |
| 5,108,412 | 4/1992 | Krumeich et al. . |
| 5,336,215 | 8/1994 | Hsueh et al. . |
| 5,549,632 | 8/1996 | Lai . |
| 5,817,115 | 10/1998 | Nigam . |
| 6,126,668 | * 10/2000 | Bair et al. ............................. 606/166 |

FOREIGN PATENT DOCUMENTS

| | | |
|---|---|---|
| 94300098 | 8/1994 | (EP) . |
| PCT/US93/10271 | 5/1994 | (WO) . |
| PCT/US94/13792 | 6/1995 | (WO) . |

* cited by examiner

*Primary Examiner*—Lee Cohen
(74) *Attorney, Agent, or Firm*—Nydegger & Associates

(57) ABSTRACT

A disposable aplanatic lens for reconfiguring the cornea of an eye for ophthalmic laser surgery includes a lens which has a flat anterior surface that is substantially parallel to a flat aplanation surface. A skirt surrounds the aplanation surface and extends outwardly therefrom to define a chamber. Additionally, the skirt is formed with a groove which creates a suction channel between the skirt and the aplanation surface in the chamber. A vacuum pump is connected in fluid communication with the suction channel and is selectively activated to create a partial vacuum in the channel. In its operation, the aplanatic lens is positioned over the cornea and the pump is activated to create the partial vacuum. Due to this partial vacuum, the cornea is drawn into the chamber where it is urged against the aplanation surface of the lens. The result of this is that the cornea is flattened into an aplanation configuration which is free from spherical aberration and coma during ophthalmic surgery.

18 Claims, 1 Drawing Sheet

CORNEAL APLANATION DEVICE

FIELD OF THE INVENTION

The present invention pertains generally to optical lenses. More particularly, the present invention pertains to surgical lenses which are used in ophthalmic laser surgery. The present invention is particularly, but not exclusively, useful as a disposable lens which can be placed in contact with the cornea of the eye to reconfigure the cornea and thereby eliminate or minimize aberrations caused by corneal geometry which otherwise distort and diminish the definition of a laser beam's focal spot.

BACKGROUND OF THE INVENTION

For ophthalmic laser procedures wherein eye tissue is to be photdisrupted or ablated, it is extremely important for the laser beam to be properly focused to a specific focal spot in the tissue that is to be affected. Also, it is extremely important that the focal spot have good definition. To do all of this, it is necessary for the laser beam to be as free from aberrations as possible. Considerations here include the eye itself, as well as the laser system. In particular, for ophthalmic laser procedures involving the cornea, it happens that the spherical geometry of the cornea introduces aberrations on its own which are separate and independent of the laser system being used. Importantly, these corneal induced aberrations distort the definition of the focal spot of the laser beam in the cornea. In order to improve this situation, these aberrations need to be eliminated or significantly minimized.

Due to the spherical geometry of the anterior surface of the cornea, two types of aberrations are of particular importance. These are: spherical aberration (which relates to points on the optical axis of the laser beam), and coma (which relates to points that are off-axis). Spherical aberration and coma are similar to each other in that they both arise from a failure to image or focus rays at the same point. Coma differs from spherical aberration, however, in that a point object is imaged not as a circle but as a comet-shaped figure (whence the term "coma"). Nevertheless, in both cases, there is a loss of definition at the focal spot.

By definition, an aplanatic lens is one which is free from both spherical aberration and coma. Still, because an interface between different media is involved, the sine condition must be considered. It then follows that aplanatic refraction results under conditions in which there is no spherical aberration or coma, and in which the sine condition is satisfied. Mathematically, the sine condition is satisfied when:

$$n_1 I_1 \sin\alpha_1 = n_2 I_2 \sin\alpha_2$$

where $n_1$ and $n_2$ are the refractive indices of the media on the laser source and focal spot sides of a media interface respectively, $I_1$ and $I_2$ are the linear dimensions of the laser source and focal spot, and $\alpha_1$ and $\alpha_2$ are the angles made with the principal axis by the conjugate portions of a ray passing between the laser source and the focal spot through the media interface.

As recognized by the present invention, aplanatic refraction at the anterior surface of the cornea can be effectively accomplished by flattening the anterior surface. With such a reconfiguration of the cornea, as a laser beam enters the cornea the sine condition will be satisfied and, importantly, the laser beam will be free of aberrations (other than chromatic) which would otherwise result from the spherical geometry of the cornea's anterior surface.

In light of the above, it is an object of the present invention to provide a disposable aplanatic lens which will reconfigure the cornea for surgical laser procedures with a disposable aplanatic configuration. Yet another object of the present invention is to provide a disposable aplanatic lens which will stabilize and maintain a proper orientation of the eye during ophthalmic laser surgery. Still another object of the present invention is to provide a disposable aplanatic lens which will beneficially reduce intraocular pressure during ophthalmic laser surgery. Another object of the present invention is to provide a disposable aplanatic lens which is easy to use, relatively simple to manufacture and comparatively cost effective.

SUMMARY OF THE INVENTION

In accordance with the present invention, an aplanatic lens for use in ophthalmic laser surgery includes an optical element in combination with a suction means. More specifically, the suction means is connected in fluid communication with the optical element to selectively create a partial vacuum between the optical element and the cornea when the aplanatic lens is positioned over an eye. In response to the partial vacuum, the cornea is urged against the optical element. This reconfigures the cornea for laser surgery and thereby eliminates or minimizes optical aberrations that would otherwise be caused by the cornea.

In more detail, the optical element of the present invention includes an aplanatic lens member which has a flat anterior surface and a flat aplanation surface. In relation to each other, the aplanation surface is oriented substantially parallel to the anterior surface. Additionally, a skirt-like structure surrounds the aplanation surface and extends outwardly therefrom to define a recessed chamber. Inside the recessed chamber, a suction channel is provided at the interface between the aplanation surface and the skirt. Preferably the optical element is made of a substantially clear, medical grade plastic.

A suction device, such as a vacuum pump, is connected in fluid communication with the recessed chamber via the suction channel. With this combination, a partial vacuum can be created in the recessed chamber whenever the opening to the chamber is covered. Specifically, as intended for the present invention, the opening to the chamber is to be covered by the cornea, and the cornea is to be drawn into the chamber where it is flattened and reconfigured to become aplanatic.

As intended for the present invention, the aplanatic lens can be mounted on a retainer ring which is attached to the laser system that is being used. More specifically, the retainer ring holds the aplanatic lens in a predetermined orientation relative to the laser system so that the laser surgery can be performed.

In the operation of the present invention, the aplanatic lens is positioned over the eye so that the cornea of the eye is covered by the opening into the recessed chamber. The suction device is then activated to create a partial vacuum in the chamber. Due to this partial vacuum, the cornea is pulled or drawn into the chamber. Several consequences result. First, the cornea is flattened against the aplanation surface of the optical element. As indicated above, with the flattening of the cornea, spherical aberrations and comas which would otherwise be caused by the spherical geometry of the cornea are effectively eliminated. Second, the reconfiguration of the cornea causes a decrease in the intraocular pressure which is beneficial during laser surgery. After the particular ophthalmic laser procedure has been completed, the suction device is deactivated, the partial vacuum is dissipated, and the aplanatic lens is removed from the eye. The aplanatic lens can be discarded and another new aplanatic lens may be used for the next patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
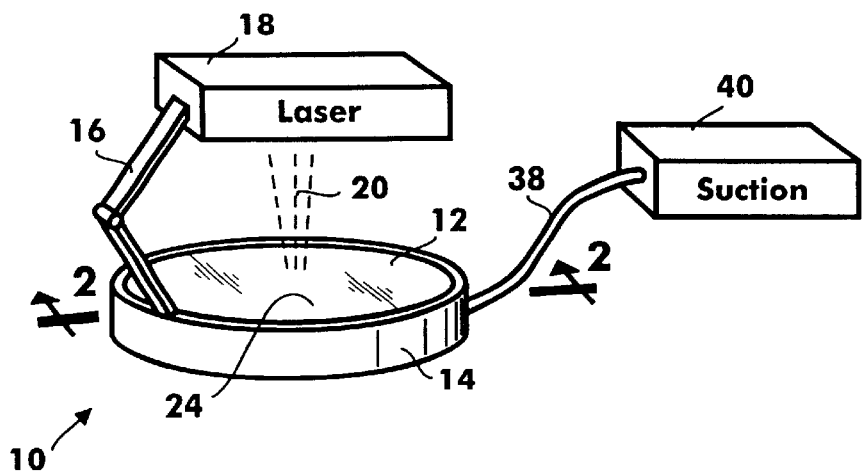
FIG. 1 is a perspective view of the aplanation lens of the present invention shown with accompanying components.

Referring initially to FIG. 1, an aplanatic lens system in accordance with the present invention is shown and generally designated 10. As shown, the system 10 includes a lens member 12 which is mounted on a retainer ring 14. Further, the retainer ring 14 is adjustably connected via an extension arm 16 to a laser source 18. For purposes of the present invention, the laser source 18 is activated to generate a laser beam 20 which is directed through the lens member 12. As will become more apparent with further disclosure, the lens member 12 is configured to eliminate, or substantially minimize any spherical aberration or coma that may otherwise have been caused by the spherical nature of the cornea 22 of an eye.

Figure 2:
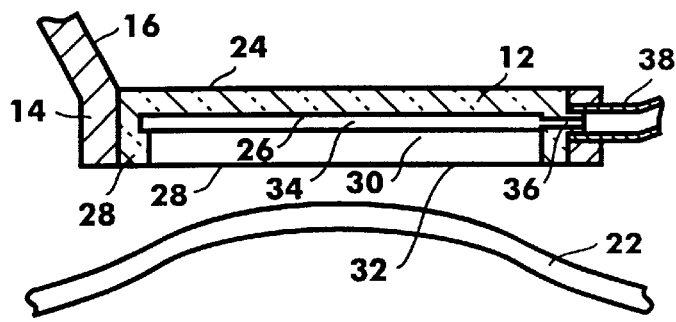
FIG. 2 is a cross-section view of the aplanation lens of the present invention as seen along the line 2—2 in FIG. 1 in position for engagement with the cornea of an eye.

The actual structure of the aplanatic lens 12 will perhaps be best appreciated by reference to FIG. 2 wherein it will be seen that the lens 12 is formed with an anterior surface 24 and an aplanation surface 26. It is to be appreciated that the anterior surface 24 is substantially flat. Likewise, the aplanation surface 26 is substantially flat. Further, the aplanation surface 26 is substantially parallel to the anterior surface 24. In FIG. 2 it will also be seen that the lens 12 is formed with a skirt 28. Specifically, the skirt 28 extends outwardly from the aplanation surface 26, as shown, and surrounds the aplanation surface 26 to create a recessed chamber 30.

Still referring to FIG. 2, it will be seen that the skirt 28 of lens member 12 establishes an opening 32 into the recessed chamber 30. Further, the lens member 12 of the present invention is formed with a suction channel 34 which surrounds the aplanation surface 26, and which is located between the skirt 28 and the aplanation surface 26. As shown, the suction channel 34 is open along its length for fluid communication with the recessed chamber 30. FIG. 2 also shows that an air passageway 36 is formed through the skirt 28 for fluid communication therethrough between a tube 38 and the suction channel 34. Consequently, tube 38 is in also in fluid communication with the recessed chamber 30. As shown in FIG. 1, a suction device 40, such as a vacuum pump, is connected with the tube 38 so that with activation of the suction device 40, a partial vacuum can be created in the recessed chamber 30 of the lens member 12.

Figure 3:
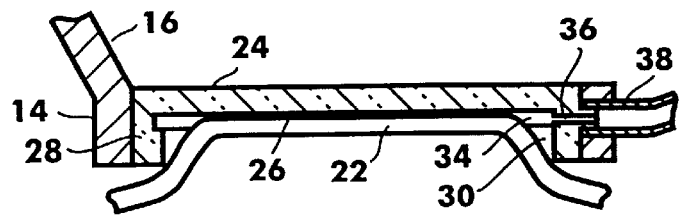
FIG. 3 is a cross-section view of the aplanation lens of the present invention as shown in FIG. 2 engaged with the cornea of an eye.

In the operation of the aplanatic lens system 10 of the present invention, the lens member 12 is first positioned above the cornea 22 of an eye substantially as shown in FIG. 2. The lens member 12 is then lowered into contact with the cornea 22 until the skirt 28 comes into contact with the cornea 22. At this point the cornea 22 completely covers the opening 32 into the recessed chamber 30. With the lens member 12 positioned on the cornea 22 as described, the suction device 40 is activated to create a partial vacuum in the recessed chamber 30. Due to the partial vacuum that is created by the suction device 40 in the recessed chamber 30, the cornea 22 is drawn or pulled into the recessed chamber 30 substantially as shown in FIG. 3. Specifically, the cornea 22 is allowed to be pulled into the recessed chamber 30 until the cornea 22 has been flattened against the aplanation surface 26 of the lens member 12. With this aplanation configuration for the cornea 22, i.e. when the cornea 22 has been flattened against the aplanation surface 26, the laser beam 20 from laser source 18 will be free from the spherical aberrations and coma which would otherwise be caused by the cornea 22.

While the particular invention as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An aplanatic lens system for use in corneal surgery which comprises:

a lens member having a substantially flat anterior surface and a substantially flat aplanation surface, said aplanation surface being substantially parallel to said anterior surface;

a skirt surrounding said aplanation surface and establishing an interface between said skirt and said aplanation surface, said skirt extending outwardly from said aplanation surface to define a recessed chamber therebetween, said recessed chamber having an opening;

a passageway in fluid communication with said recessed chamber adjacent said interface;

suction means in fluid communication with said passageway for creating a partial vacuum in said recessed chamber between said aplanation surface and the cornea to flatten the cornea against said aplanation surface when the cornea is positioned over said opening to said recessed chamber; and a retainer ring, said lens member being mounted on said retainer ring and further, wherein said retainer ring is attached to a laser system.

2. A system as recited in claim 1 wherein said skirt is formed with a groove to establish a suction channel between said aplanation surface and said skirt, said suction channel in fluid communication with said passageway.

3. A system as recited in claim 1 wherein said suction means is a pump.

4. A system as recited in claim 1 wherein said lens member is made of a medical grade plastic.

5. A system as recited in claim 1 wherein said skirt is integral with said lens member.

6. A device for reconfiguring a cornea for ophthalmic laser surgery which comprises:

an optical element having an anterior surface and a posterior surface, said posterior surface being formed with a recessed chamber, a portion of said posterior surface being an aplanation surface; and suction means connected in fluid communication with said recessed chamber, said suction means positioned adjacent said aplanation surface to draw the cornea into the chamber and reconfigure the cornea into an aplanatic configuration in said recessed chamber.

7. A device as recited in claim 6 wherein said anterior surface is substantially flat.

8. A device as recited in claim 7 wherein said aplanation surface is flat and substantially parallel to said anterior surface.

9. A device as recited in claim 8 wherein said aplanation configuration results when the cornea is flattened against said aplanation surface.

10. A device as recited in claim 8 wherein said posterior surface is formed with a groove adjacent said aplanation surface to establish a suction channel.

11. A device as recited in claim 10 wherein said suction means is connected in fluid communication with said recessed chamber through said suction channel.

12. A device as recited in claim 8 wherein said suction means is a pump.

13. A device as recited in claim 8 wherein said optical element is made of a clear medical grade plastic.

14. A device as recited in claim 6 further comprising a retainer ring, said optical element being mounted on said retainer ring and further, wherein said retainer ring is attached to a laser system.

15. A method for reconfiguring a cornea for ophthalmic laser surgery which comprises the steps of:

providing an aplanatic lens which includes a lens member having a substantially flat anterior surface and a substantially flat aplanation surface, said aplanation surface being substantially parallel to said anterior surface, and said lens having a skirt surrounding said aplanation surface and establishing an interface between said skirt and said aplanation surface, said skirt extending outwardly from said aplanation surface to define a recessed chamber therebetween, said recessed chamber having an opening and said lens further having a passageway in fluid communication with said recessed chamber adjacent said interface, and a suction means in fluid communication with said passageway for creating a partial vacuum in said recessed chamber between said aplanation surface and the cornea;

positioning said opening to said recessed chamber of said aplanatic lens over the cornea; and creating a partial vacuum in said recessed chamber with said suction means to draw the cornea into the recessed chamber through said opening to flatten the cornea against said aplanation surface into an aplanation configuration.

16. A method as recited in claim 15 wherein said suction means is a pump and said creating step is accomplished by selectively activating said pump.

17. A method as recited in claim 15 wherein said skirt is formed with a groove to establish a suction channel between said aplanation surface and said skirt, wherein said passageway is connected in fluid communication with said suction channel.

18. A method as recited in claim 15 wherein said creating step reduces intraocular pressure in the eye behind the cornea.

\* \* \* \* \*